United States Patent
Jacobs et al.

(10) Patent No.: US 9,918,857 B2
(45) Date of Patent: Mar. 20, 2018

(54) SCAFFOLD HAVING A SHAPED STRUT AND METHODS FOR SHAPING SCAFFOLD STRUTS

(71) Applicant: Abbott Cardiovascular Systems Inc., Santa Clara, CA (US)

(72) Inventors: Jamey Jacobs, Danville, CA (US); Stephen Pacetti, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 254 days.

(21) Appl. No.: 14/615,314

(22) Filed: Feb. 5, 2015

(65) Prior Publication Data

US 2016/0200035 A1    Jul. 14, 2016

Related U.S. Application Data

(60) Provisional application No. 62/103,470, filed on Jan. 14, 2015.

(51) Int. Cl.
*A61F 2/06* (2013.01)
*A61F 2/915* (2013.01)
(Continued)

(52) U.S. Cl.
CPC .............. *A61F 2/915* (2013.01); *A61L 31/06* (2013.01); *A61L 31/14* (2013.01); *B29C 59/085* (2013.01);
(Continued)

(58) Field of Classification Search
CPC ................. A61F 2/82; A61F 2002/821; A61F 2002/823; A61F 2/848; A61F 2002/8483; A61F 2002/8486; A61F 2/86; A61F 2/88; A61F 2/885; A61F 2/89; A61F 2/90; A61F 2/91; A61F 2/915; A61F 2002/91508; A61F 2002/91516; A61F 2002/91525; A61F 2002/91533; A61F 2002/91541; A61F 2002/9155; A61F 2002/91558; A61F 2002/91566; A61F 2002/91575; A61F 2002/91583
See application file for complete search history.

(56) References Cited

U.S. PATENT DOCUMENTS 5,746,691 A    5/1998  Frantzen
6,120,847 A    9/2000  Yang et al.
(Continued)

FOREIGN PATENT DOCUMENTS

EP    1 779817    5/2007

OTHER PUBLICATIONS

Kolachalama et al., "Luminal flow patterns dictate arterial drug deposition in stent-based delivery", J. Control Release 133 (5) 20 pgs. (2009).
(Continued)

*Primary Examiner* — Jonathan Miles
(74) *Attorney, Agent, or Firm* — Squire Patton Boggs (US) LLP (57) ABSTRACT

A scaffold strut is shaped to improve hemocompatibility. After laser cutting, the scaffold is placed on a work piece and its struts are shaped by flame polishing or brushing. The abluminal surfaces and luminal surfaces can have corners rounded. The strut can have a sloped surface on its luminal side without reducing strut thickness needed for strength.

13 Claims, 8 Drawing Sheets

(51) Int. Cl.

| | | |
|---|---|---|
| *B29C 59/08* | (2006.01) | |
| *A61L 31/06* | (2006.01) | |
| *A61L 31/14* | (2006.01) | |
| *A61F 2/958* | (2013.01) | |
| *B29K 67/00* | (2006.01) | |
| *B29L 31/00* | (2006.01) | |

(52) U.S. Cl.
CPC ..... *A61F 2/958* (2013.01); *A61F 2002/91575* (2013.01); *A61F 2210/0004* (2013.01); *A61F 2230/0004* (2013.01); *A61F 2240/001* (2013.01); *A61F 2250/0036* (2013.01); *B29K 2067/046* (2013.01); *B29K 2995/006* (2013.01); *B29L 2031/7534* (2013.01)

(56) References Cited

U.S. PATENT DOCUMENTS

| | | |
|---|---|---|
| 6,685,737 B1 | 2/2004 | Pacetti |
| 7,658,880 B2 | 2/2010 | Wu |
| 8,002,817 B2 | 8/2011 | Limon |
| 8,303,644 B2 | 11/2012 | Lord et al. |
| 8,388,673 B2 | 3/2013 | Yang et al. |
| 8,580,180 B2 | 11/2013 | Wu |
| 8,795,030 B2 | 8/2014 | Huang et al. |
| 2006/0095123 A1 | 5/2006 | Flanagan |
| 2006/0136048 A1 | 6/2006 | Pacetti |
| 2008/0262607 A1 | 10/2008 | Fricke |
| 2010/0049300 A1 | 2/2010 | Harder |
| 2011/0028072 A1 | 2/2011 | Huang et al. |
| 2012/0042501 A1 | 2/2012 | Wang et al. |
| 2012/0071962 A1* | 3/2012 | Huang ............... A61F 2/91 623/1.16 |

OTHER PUBLICATIONS

Kolandaivelu et al., "Stent Thrombogenicity early in high-risk interventional settings is driven by stent design and deployment and protected by polymer-drug coatings", Circulation 123, pp. 1400-1409 (2011).

Written Opinion and the International Search Report for International Patent Application No. PCT/US2016/013268, dated Apr. 28, 2016.

* cited by examiner

SCAFFOLD HAVING A SHAPED STRUT AND METHODS FOR SHAPING SCAFFOLD STRUTS

This application claims priority to U.S. provisional application No. 62/103,470 filed Jan. 14, 2015.

BACKGROUND OF THE INVENTION

Field of the Invention

The present invention relates to bioresorbable scaffolds; more particularly, this invention relates to bioresorbable scaffolds for treating an anatomical lumen of the body.

Description of the State of the Art

Radially expandable endoprostheses are artificial devices adapted to be implanted in an anatomical lumen. An "anatomical lumen" refers to a cavity or duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents hold open and reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into the anatomical lumen, advancing the catheter in the anatomical lumen to a desired treatment location, expanding the stent at the treatment location, and removing the catheter from the lumen.

The following terminology is used. When reference is made to a "stent", this term will refer to a permanent structure, usually comprised of a metal or metal alloy, generally speaking, while a scaffold will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure.

Scaffolds and stents traditionally fall into two general categories—balloon expanded and self-expanding. The later type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively no plastic or inelastic deformation when stowed in a sheath or expanded within a lumen (with or without an assisting balloon). Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris-type or other form of crimper, such as the crimping machine disclosed and illustrated in US 2012/0042501. A significant amount of plastic or inelastic deformation occurs both when the balloon expandable stent or scaffold is crimped and later deployed by a balloon. At the treatment site within the lumen, the stent is expanded by inflating the balloon.

The stent must be able to satisfy a number of basic, functional requirements. The stent (or scaffold) must be capable of sustaining radial compressive forces as it supports walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to heal or remodel, after which the stent is no longer needed.

The present application adopts the following definitions of radial strength and radial stiffness. Radial strength, which is the ability of a stent to resist radial compressive forces, relates to a stent's radial yield strength around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation. A radial "stiffness" refers to the amount net radial inward force (i.e., uniform radial inward pressure over the entire abluminal scaffold surface x the abluminal surface area) required to reversibly decrease a scaffold diameter by a certain amount. The slope of the curve from a force-deflection plot will be called the "absolute stiffness" or K. The units are N/mm and the stiffness is expressed for the linearly elastic range of response to the radial force. Thus, for a scaffold deployed to 6.5 mm and having a linear elastic range for radial compression between 6.5 mm and 5.5 mm and a radial stiffness of 20 N/mm, a net inward radial inward force of 10 N is needed to decrease the scaffold diameter from 6.5 mm to 6.0 mm. After the radial force is removed, the scaffold returns to the 6.5 mm diameter.

Figure 1:
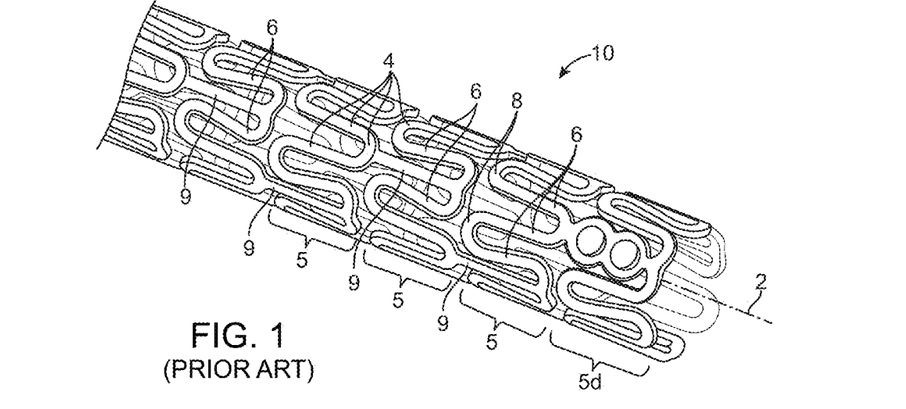
FIG. 1 is a perspective view of a portion of a prior art scaffold. The scaffold is shown in a crimped state (balloon not shown).

Scaffolds have been made from a bioresorbable polymer. Examples of bioresorbable polymer scaffolds include those described in U.S. Pat. No. 8,002,817 to Limon, U.S. Pat. No. 8,303,644 to Lord, and U.S. Pat. No. 8,388,673 to Yang. FIG. 1 shows an end segment of a bioresorbable polymer scaffold designed for delivery through anatomical lumen using a catheter and plastically expanded using a balloon. The scaffold has a cylindrical shape having a central axis 2 and includes a pattern of interconnecting structural elements, which will be called bar arms or struts 4. Axis 2 extends through the center of the cylindrical shape formed by the struts 4. The stresses involved during compression and deployment are generally distributed throughout the struts 4 but are focused at the bending elements, crowns or strut junctions. Struts 4 include a series of ring struts 6 that are connected to each other at crowns 8. Ring struts 6 and crowns 8 form sinusoidal rings 5. Rings 5 are arranged longitudinally and centered on an axis 2. Struts 4 also include link struts 9 that connect rings 5 to each other. Rings 5 and link struts 9 collectively form a tubular scaffold 10 having axis 2 representing a bore or longitudinal axis of the scaffold 10. Ring 5d is located at a distal end of the scaffold. Crowns 8 form smaller angles when the scaffold 10 is crimped to a balloon and larger angles when plastically expanded by the balloon. After deployment, the scaffold is subjected to static and cyclic compressive loads from surrounding tissue. Rings 5 are configured to maintain the scaffold's radially expanded state after deployment.

Scaffolds may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away when implanted. The scaffold, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stent thrombosis and disease progression that can require another revascularization. In these cases, there is a desire to treat a vessel using a polymer scaffold, in particular a bioabsorable or bioresorbable polymer scaffold, as opposed to a metal stent, so that the prosthesis's presence in the vessel is temporary.

Polymeric materials considered for use as a polymeric scaffold, e.g. poly(L-lactide) ("PLLA"), poly(L-lactide-co-glycolide) ("PLGA"), poly(D-lactide-co-glycolide) or poly (L-lactide-co-D-lactide) ("PLLA-co-PDLA") with less than 10% D-lactide, poly(L-lactide-co-caprolactone) (PLLA-PCL) and PLLD/PDLA stereo complex, may be described, through comparison with a metallic material used to form a stent, in some of the following ways. Compared to metals and alloys, the suitable polymers have a lower strength to volume ratio, which means more material is needed to provide an equivalent mechanical property. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymers such as PLLA or PLGA.

Intravascular drug eluting scaffolds and stents must fulfill many criteria simultaneously. In addition to the aforementioned acute mechanical demands for radial support, scaffolding, and expansion capability, the stent or scaffold must meet a pharmaceutical function of controlled drug release to prevent neointimal hyperplasia and its consequence of restenosis. While accomplishing this, there are many goals for biocompatibility. Intravascular scaffolds start as blood contacting devices. With time they become encapsulated in the vessel wall where they undergo a benign process of resorption. There is both the biocompatibility required for blood contact and the necessary compatibility with vascular tissue.

There is a continuing need to improve the biocompatibility of a scaffold; in particular, there is a continuing need to improve upon on the biocompatibility of a scaffold shortly following implantation when a significant portion of the structure is in contact with blood passing through the vessel.

SUMMARY OF THE INVENTION

What is disclosed is a polymeric, bioresorbable scaffold with rounded, hemodynamic struts and techniques for making shaped struts for such a scaffold. The scaffold material includes a bioresorbable, polyester polymer.

In preferred embodiments, extrusion, injection molding, or dip coating on a mandrel may be used to form a tube. The polymer may be a bioresorbable polymer such as PLLA or blend. The tube may be annealed or expanded/drawn to orient the polymer. The tube is then cut by a laser to form a scaffold pattern, such as the pattern shown in FIG. 1. Methods are then employed to shape scaffold struts. Rounded or shaped strut corners should produce more hemodynamic struts in cross section.

Blood compatibility, also known as hemocompatibility or thromboresistance, is a desired property for scaffolds and stents. The adverse event of scaffold thrombosis, while a very low frequency event, carries with it a high incidence of morbidity and mortality. To mitigate the risk of thrombosis, dual anti-platelet therapy is administered with all coronary scaffold and stent implantation. This is to reduce thrombus formation due to the procedure, vessel injury, and the implant itself. Scaffolds and stents are foreign bodies and they all have some degree of thrombogenicity. The thrombogenicity of a scaffold refers to its propensity to form thrombus and this is due to several factors, including strut thickness, strut width, strut shape, total scaffold surface area, scaffold pattern, scaffold length, scaffold diameter, surface roughness and surface chemistry. Some of these factors are interrelated. The effect of strut thickness on acute thrombogenicity has been documented and studied both in vivo and in silico. A scaffold should also occupy the minimum volume needed to meet the radial strength goals. Consequently, the strut thickness, strut width, and total surface area of a scaffold have multiple constraints, in addition to the influence of these dimensions on its profile and hence its hemocompatibility.

Figure 2:
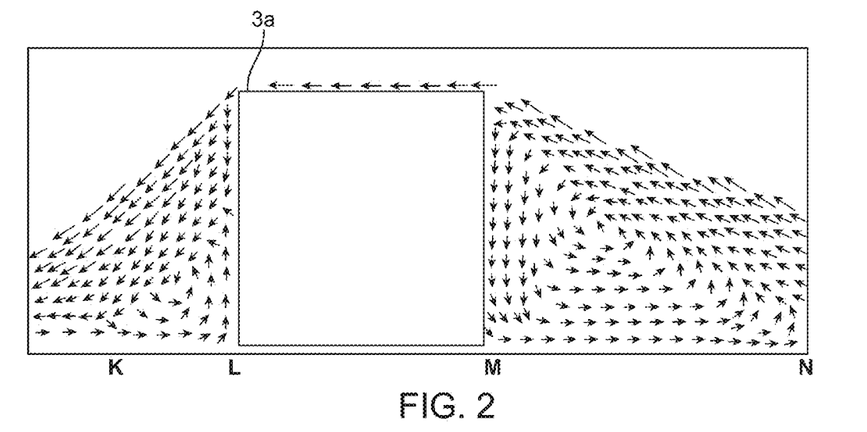
FIG. 2 shows fluid streamlines adjacent a square-cross-section of a scaffold strut. The streamlines show zones of fluid recirculation upstream and downstream of the strut.

Computational fluid mechanics analyses have shown that struts with square cross sections are not ideally hemodynamic and have large recirculating zones on both sides of the strut. FIG. 2 shows a steady-state flow (Reynolds Number of 282) around a square 3a strut. As shown by the arrows there are recirculation zones to the left and to the right of the stent strut. Footprints of these zones (KL and MN, respectively) are shown. Shown is a laminar flow condition for the stent strut 3a. The recirculating zones are regions where platelets have long residence time and will be prone to form thrombus.

Figure 3A:
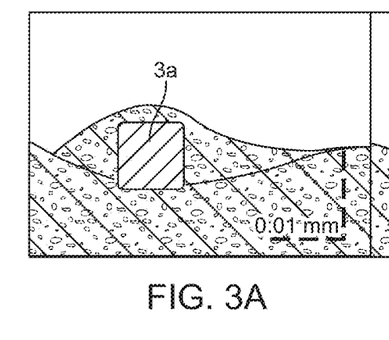
FIG. 3A is a cross-sectional view of a thin strut of scaffold based on an explant of an implanted scaffold from a porcine model.
Figure 3B:
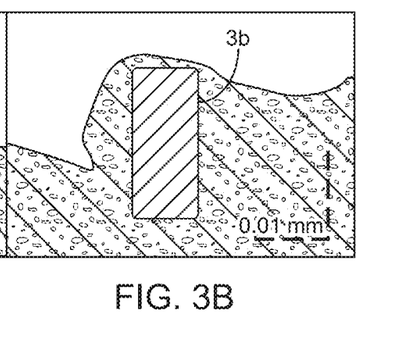
FIG. 3B is a cross-sectional view of a thick strut of scaffold based on an explant of an implanted scaffold from a porcine model.
Figure 4:
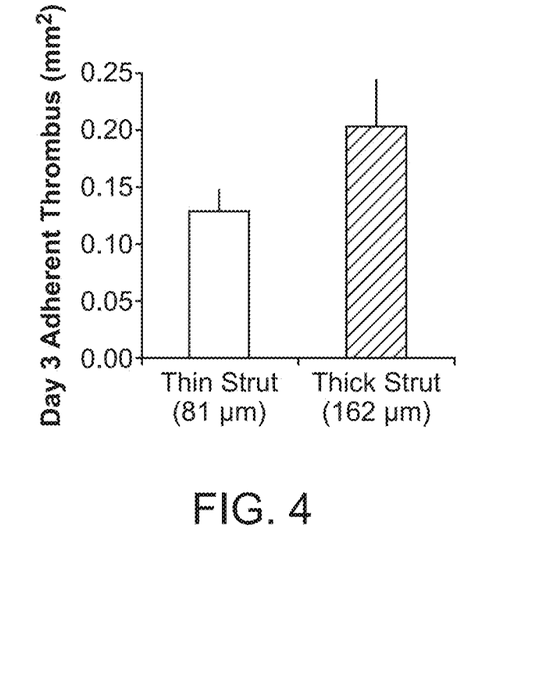
FIG. 4 compares the Adherent Thrombus area of the thin verses thick struts depicted in FIGS. 3A and 3B.
Figure 5:
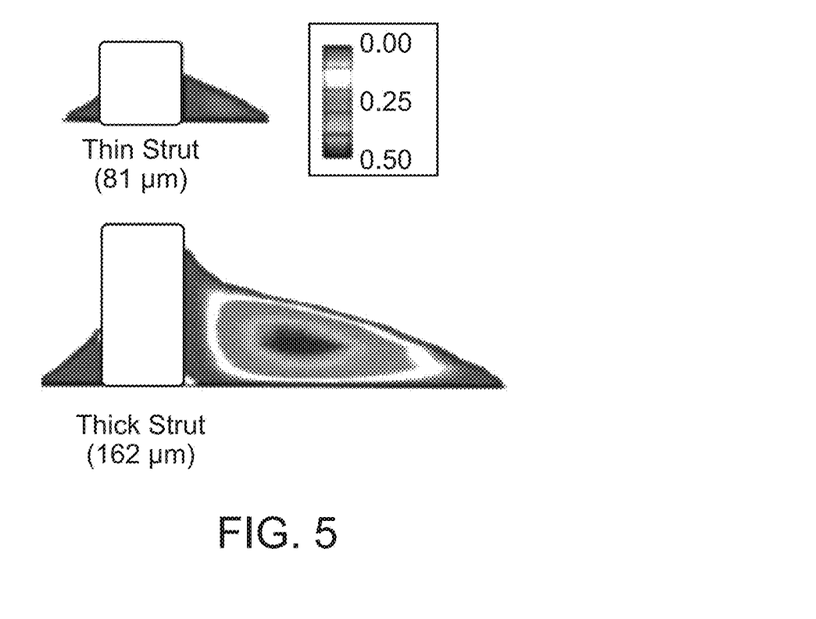
FIG. 5 describes using computational fluid dynamics to model fluid flow immediately upstream and downstream of the thin and thick struts for a scaffold.

FIGS. 3A-3B depict experimental results from porcine models for a thin strut (81 microns, μm) and thick strut (162 microns, μm). The drawings, based on histological images taken from explants (3 days after implantation), show in vivo thrombogenicity for the thin struts verses thick struts for porcine coronary arteries (n=6 for each). FIG. 4 shows results from a morphometric analysis of adherent thrombus area as assessed through histomorphometric measurement of stented sections of the porcine coronary artery. As shown there is a significant increase in the adherent thrombus when the strut thickness doubles in size. That is, there is a significant increase downstream of the strut when the strut thickness doubles in size. FIG. 5 is a computational fluid dynamics model prediction of the flow alterations surrounding the thin and thick struts (units are cm/sec). With regards to thrombogenicity of the scaffold in the artery, the most important factors are the minimum lumen diameter (MLD) or diameter of residual stenosis in the scaffold, degree of scaffold malapposition, strut thickness and strut shape. FIGS. 2-5 evidence that strut thickness has a direct effect on thrombogenicity. Although not a primary contributor, thick struts do play a role.

As alluded to above, the strut must have a certain minimum dimensions (or volume) in order to have adequate strength. Thus, there is a constraint on how thin one can make a strut while maintaining a desired radial strength. However, it will be appreciated that alternative to making a strut more thin, one can instead employ techniques to shape the strut so that it becomes more hemodynamic. Hence, the profile (thickness) of the strut to flow can be similar or the same as an existing strut thickness (thereby maintaining strength characteristics for the strut, e.g., flexural rigidity) but the stagnant flow downstream of the strut can be reduced significantly. Thus, by shaping the strut so as to produce a more hemodynamic strut, the thrombogenicity caused by disturbed blood flow can be reduced. In one example more rounded struts are made by shaping a rectangular strut cut from a tube.

In accordance with these objectives, there is a method for shaping a strut using a torch, flame, or a brush. According to these methods there is a first, second and third type of shaped strut that may be made. These struts are more hemodynamic without a significant, if any reduction in strut overall thickness.

According to one aspect of the invention, there is a scaffold, medical device, method for making such a scaffold, or method for assembly of a medical device comprising such a scaffold having one or more, or any combination of the following items (1) through (18):

(1) a polymer scaffold made from a tube;
(2) a shaped strut of the scaffold;
(3) a shaped strut having one, two, three or four rounded or smoothed corners;
(4) a shaped strut that is in cross section symmetric about two axes passing through a centroid of the strut, about one axis passing through the centroid, or not symmetric about any axis passing through the centroid;
(5) any shaped strut embodiments described in connection with FIG. 8A, 8B or 8C;
(6) a shaped strut having a straight, linear or constant taper from a leading to trailing edge thereof; or a curved, non-linear or varying taper form a leading to trailing edge thereof;
(7) a shaped strut having a thickness at a trailing edge that is 20% to 60% or 50% to 80%, or 20 to 80% of a maximum thickness, or a thickness at the leading edge thereof
(8) a strut shaped by flame polishing, brushing or a combination of the two;
(9) a scaffold crimped on a balloon and a scaffold strut has a first type, second type or third type of shaped strut;
(10) An aspect ratio (AR) of strut width (w) to strut thickness (t) (AR=w/t) at a strut cross-section is between 0.5 to 1.5, 0.7 to 1.5, 0.7 to 1.3, 0.9 to 1.5, 0.9 to 1.2, 1.0 to 1.5, 1.5 to 2.0, 1.5 to 3.0, 1.5 to 4.0, or 1.0 to 4.0. Both w and t are measured at the same cross-section. The AR can be the ratio of the minimum width to the minimum thickness for the cross-section, or the AR can be the ratio of the maximum width to the maximum thickness for the cross-section. The AR can refer to the AR of a strut before the strut is shaped, e.g., rectangular strut cross-section, after the strut is shaped, e.g., FIG. 8A, 8B or 8C, or the AR can refer to both, as in the case of the AR being measured with respect to the maximum width and thickness of the shaped strut, which width and thickness is about the same as the width and thickness of the rectangular strut.
(11) A strut thickness (or wall thickness of a tube from which a strut is made) for a scaffold (pre-crimp diameter of 2.5 to 5 mm) is less than 175 microns, less than 150 microns, less than 140 microns, less than 130 microns, about 100 microns, 80 to 100 microns, 80 to 120 microns, 90 to 100 microns, 90 to 110 microns, or 95 to 105 microns. More preferably a strut or wall thickness is between 80 and 100 microns, and more preferably between 90 and 105 microns; and
(12) A strut thickness for a scaffold (pre-crimp diameter of 7 to 10 mm) is less than 280 microns, less than 260 microns, less than 240 microns, about 190 micron, 149 to 186 microns, 149 to 220 microns, 170 to 190 microns, 170 to 210 microns, 210 to 220 microns. More preferably a strut thickness is between 150 and 190 microns for a scaffold having an outer diameter of 7, 8 or 9 mm.
(13) A method for making a medical device, comprising: forming a polymer scaffold having struts; and flame polishing the scaffold to form shaped struts.
(14) The method of (13) in combination with one or more of, or any combination of the following things: wherein the forming the polymer scaffold includes cutting a scaffold pattern from a tube comprising a polymer material, wherein prior to the flame polishing a scaffold strut has sharp or right angle corners, and wherein the flame polishing further includes disposing a torch having a flame at a distance from the strut and moving the flame over the strut at a rate sufficient to melt the material such that surface tension at the scaffold surface causes the sharp or right angle corners to become rounded; wherein the flame polishing further includes: placing the scaffold on an apparatus, the apparatus including a mandrel and a linear actuator, and using the linear actuator and mandrel to displace the scaffold and rotate the scaffold about a longitudinal axis, respectively, relative to the flame; wherein the flame is disposed closer to an abluminal surface of the scaffold than a luminal surface, to thereby make corners bordering abluminal strut surfaces more rounded than corners bordering luminal surfaces; wherein the flame is disposed closer to a luminal surface of the scaffold than an abluminal surface, to thereby make corners bordering luminal strut surfaces more rounded than corners bordering abluminal surfaces; wherein the scaffold has a bore and the flame is passed through the bore to induce rounding of the corners bordering luminal strut surfaces; wherein parameters for flame polishing comprise: a flame temperature of between about 1500° C. and 5000° C., a torch fuel selected form the set consisting of Hydrogen, methane, ethane, propane, butane, pentane, hexane, heptane, octane, nonane, decane, methanol, ethanol, acetylene, gasoline, kerosene, fuel oil with oxidizers of air or oxygen, a rate and distance of the flame passed over the scaffold is about 0.5-30 mm/sec and about 2-40 mm, respectively, and a flame size is about 2-20 mm; wherein the strut having the rounded corners is in cross section symmetric about two orthogonal axes or only one orthogonal axis; and/or wherein the strut having the rounded corners has a thickness and a width, a left and right side, and a luminal and an abluminal surface, and wherein the strut having the rounded corners is, in respect to a cross-section of the strut symmetric about a first axis that passes through the strut centroid, the strut luminal and abluminal surfaces but not the left and right sides, and asymmetric about a second axis that passes through the strut centroid, the left and right sides but not the strut luminal and abluminal surfaces.

(15) A method for making a medical device, comprising: forming a polymer scaffold having struts; and brushing the scaffold to form shaped struts.

(16) The method of (15) in combination with one of more of, or any combination of the following things: wherein the forming the polymer scaffold includes cutting a scaffold pattern from a tube comprising a polymer material, wherein prior to the brushing a scaffold strut has sharp or right angle corners, the brushing further including disposing a brush having bristles over the scaffold and pulling or pushing the brush over a surface of the strut to cause the bristles to abrade the strut surface, thereby causing the sharp or right angle corners to become rounded; wherein the brush is tubular with bristles extending radially inwards towards the brush bore, and the brush is pulled or pushed over abluminal surfaces of the scaffold; wherein the scaffold has a bore and the brush is pushed or pulled through the bore to abrade corners bordering the luminal surfaces of the scaffold; wherein the strut has a thickness and a width and the bristles have a diameter that is less than the thickness and the width; wherein the brush comprises wires, a wire comprising: a length between 500 and 8000 microns, a mean roughness (Ra) between 0.1 and 20 microns, a wire material is metal, metal alloy, polymer, polymer containing an abrasive, ceramic, or glass, and a diameter between about 1 to 200 microns, about 2 to 150 microns or between about 10 to 100 microns; wherein the strut having the rounded corners is in cross section symmetric about two orthogonal axes, only one orthogonal axis or is not symmetric about two orthogonal axes passing through a centroid of the strut cross-section; wherein the strut having the rounded corners has a thickness and a width, a left and right side, and a luminal and an abluminal surface, wherein the strut having the rounded corners is symmetric about a first axis that passes through the luminal and abluminal surfaces but not the left and right sides, and wherein the strut is asymmetric about a second axis that passes through the left and right sides but not the luminal and abluminal surfaces; or wherein the strut having the rounded corners is asymmetric about both the first and second axes; and/or wherein the strut having the rounded corners has a linear or non-linear taper from a leading to a trailing edge thereof, and/or the strut thickness at the trailing edge is between about 20% to 60% less than a maximum strut thickness or the strut thickness at the leading edge.

(17) A medical device, comprising: a balloon catheter including a balloon disposed at a distal end of the catheter; and a polymer scaffold crimped to the balloon, the scaffold having a pattern of shaped struts, wherein a shaped strut has a leading edge, a trailing edge, a luminal surface facing a surface of the balloon and an abluminal surface facing away from the balloon surface; wherein the shaped strut is, in respect to a cross section of the strut, asymmetric about each of two orthogonal axes passing through a centroid of the strut cross-section.

(18) The polymer scaffold of (17) made according to the method of (15) or (16).

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION

In the description like reference numbers appearing in the drawings and description designate corresponding or like elements among the different views.

For purposes of this disclosure, the following terms and definitions apply:

The terms "about" or "approximately" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

A "stent" means a permanent, durable or non-degrading structure, usually comprised of a non-degrading metal or metal alloy structure, generally speaking, while a "scaffold" means a temporary structure comprising a bioresorbable, biodegradable, or bioerodable polymer, metal or combination thereof and capable of radially supporting a vessel for a limited period of time, e.g., 3, 6 or 12 months following implantation. It is understood, however, that the art sometimes uses the term "stent" when referring to either type of structure.

"Inflated diameter" or "expanded diameter" refers to the inner diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon (i.e., a balloon having a 6.5 mm nominal diameter when inflated to a nominal balloon pressure such as 6 times atmospheric pressure) has about a 7.4 mm post-dilation diameter, or a 6.0 mm balloon has about a 6.5 mm post-dilation diameter. The nominal to post dilation ratios for a balloon may range from 1.05 to 1.7 (i.e., a post-dilation diameter may be 5% to 70% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

"Post-dilation diameter" (PDD) of a scaffold refers to the inner diameter of the scaffold after being increased to its expanded diameter and the balloon removed from the patient's vasculature. The PDD accounts for the effects of recoil. For example, an acute PDD refers to the inner scaffold diameter that accounts for an acute recoil in the scaffold.

A "pre-crimp diameter" means an outer diameter (OD) of a tube from which the scaffold was made (e.g., the scaffold is cut from a dip coated, injection molded, extruded, radially expanded, die drawn, and/or annealed tube) or the scaffold before it is crimped to a balloon. Similarly, a "crimped diameter" means the OD of the scaffold when crimped to a balloon. The "pre-crimp diameter" can be about 2 to 2.5, 2 to 2.3, 2.3, 2, 2.5, 3.0 times greater than the crimped diameter and about 0.9, 1.0, 1.1, 1.3 and about 1-1.5 times higher than an expanded diameter, the nominal balloon diameter, or post-dilation diameter. Crimping, for purposes of this disclosure, means a diameter reduction of a scaffold characterized by a significant plastic deformation, i.e., more than 10%, or more than 50% of the diameter reduction is attributed to plastic deformation, such as at a crown in the case of a stent or scaffold that has an undulating ring pattern, e.g., FIG. 1. When the scaffold is deployed or expanded by the balloon, the inflated balloon plastically deforms the scaffold from its crimped diameter. Methods for crimping scaffolds made according to the disclosure are described in US20130255853.

A "centroid" is a center of area of a body in cross-section. It is analogous to a center of mass for a body, except that it refers to a center of a two-dimensional area. A centroid (X) for a strut is $X=(1/A)(\Sigma x_i \cdot A_i, i=1 \ldots n)$ where the sum is taken over the entire two-dimensional area ($i=1 \ldots n$) of the strut cross-section, "A" is the total area ($A=\Sigma A_i, i=1 \ldots n$) of the strut cross-section and the product $x_i \cdot A_i$ is a first moment of area for an area element $A_i$ of the strut cross-section located a distance $x_i$ from some reference, e.g., a coordinate system origin or a strut corner before the strut is shaped.

Figure 6:
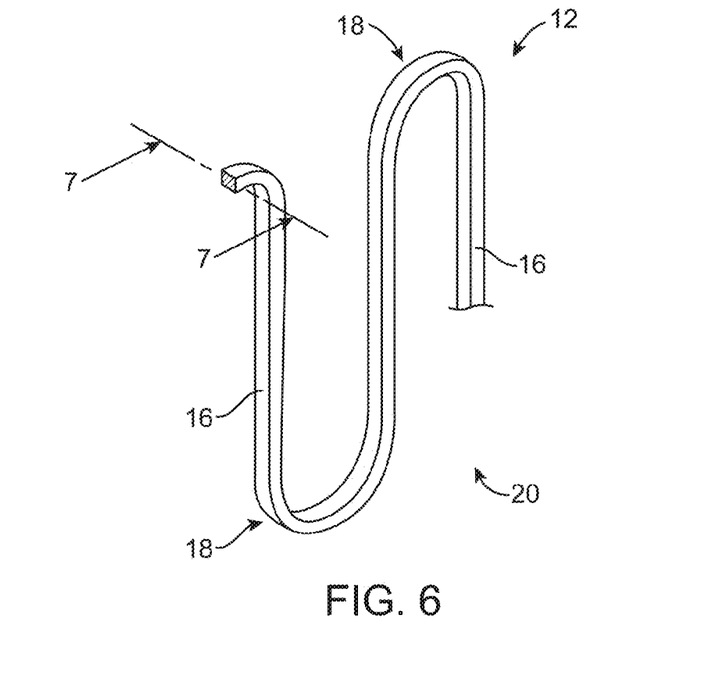
FIG. 6 is a perspective view of a portion of a scaffold ring that includes a crown and strut.

Shown in FIG. 6 is a portion of a ring 20 from a scaffold, such as the scaffold shown in FIG. 1. The ring 20 is made up of struts 16 that are joined at crowns 18.

Figure 7:
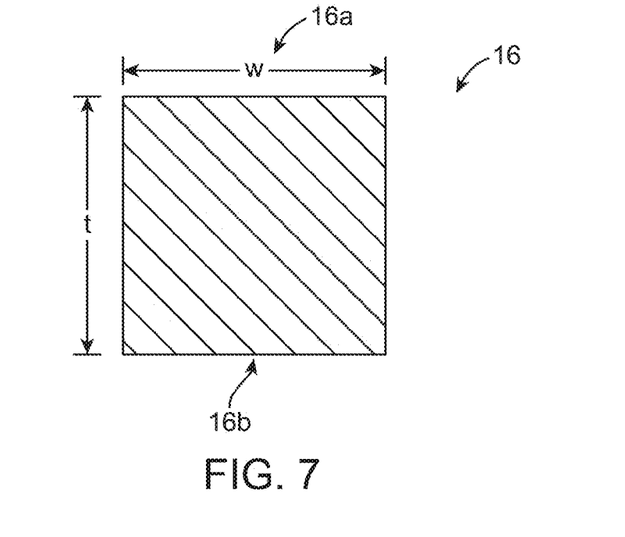
FIG. 7 shows a cross-section of the strut from FIG. 6, taken at section 7-7.

FIG. 7 is a cross sectional view of the strut 16 from FIG. 6. In this example the strut is shown as square, but more generally the strut 16 cross-section is rectangular. The dimensions of the cross-section will be designated as thickness (t)×width (w) as illustrated. In some embodiments the strut thickness (t) corresponds to a wall thickness of a tube from which the strut was made using a laser. An aspect ratio (AR) of strut width to wall thickness (AR=w/t) may range between 0.5 to 1.5, 0.7 to 1.5, 0.7 to 1.3, 0.9 to 1.5, 0.9 to 1.2, 1.0 to 1.5 or 1.5 to 2.0.

The wall thickness can vary based on a pre-crimp diameter. In some embodiments, a wall thickness for a scaffold having a 3 mm outer diameter includes less than 175 microns, less than 150 microns, less than 140 microns, less than 130 microns, about 100 micron, 80 to 100 microns, 80 to 120 microns, 90 to 100 microns, 90 to 110 microns, 110 to 120 microns, or 95 to 105 microns. More preferably a wall thickness is between 80 and 100 microns, and more preferably between 85 and 95 microns. A wall thickness for a scaffold having 7, 8 or 9 mm outer diameters include less than 280 microns, less than 260 microns, less than 240 microns, about 190 micron, 149 to 186 microns, 149 to 220 microns, 170 to 190 microns, 170 to 210 microns, 210 to 220 microns. More preferably a wall thickness is between 150 and 190 microns for a scaffold having an outer diameter of 7, 8 or 9 mm.

The width (w) dimension spans a width-wise extent of the strut's luminal 16a and abluminal 16b surface for the scaffold. Thus, when the scaffold is implanted, the surface 16a (luminal) faces the lumen interior and comes in contact with blood flowing through the lumen. The surface 16b (abluminal) faces and is in intimate contact with the walls of the vessel.

In general it is understood that the surfaces 16a, 16b may be considered flat when the strut is made from a tube 16 because the tube's radius is typically much, much larger than the width-wise extent of the abluminal and luminal surfaces 16a, 16b. In the preferred embodiments the scaffold is made from a tube that has a diameter about equal to, or greater than a nominal balloon diameter of the balloon upon which the scaffold is attached. Struts of some stents formed at a diameter very close to a crimped diameter may have curvature on the abluminal/luminal side.

Following the laser cutting, the strut cross-section takes the general shape of a rectangle, e.g., square, cross-section having relatively sharp or right-angle corners as shown. While metallic stents nearly always undergo electropolishing which rounds the strut corners, bioresorbable polymeric scaffolds do not require a polishing operation. Hence such scaffolds can have struts with sharp corners.

In accordance with the objectives of the invention, methods are disclosed for re-shaping the strut 16 of the scaffold including, but limited to methods for rounding corners of struts of a scaffold to improve the hemocompatibility of the scaffold when implanted in a vessel. According to one aspect of the disclosure, the methods employed may be used to produce three types of struts having a shaped cross-section, or three types of shaped struts (the term "shaped strut" means a strut of a scaffold cut from a tube. The strut surface is changed by an abrasive or melting process that produces at least one rounded corner).

Figure 8A:
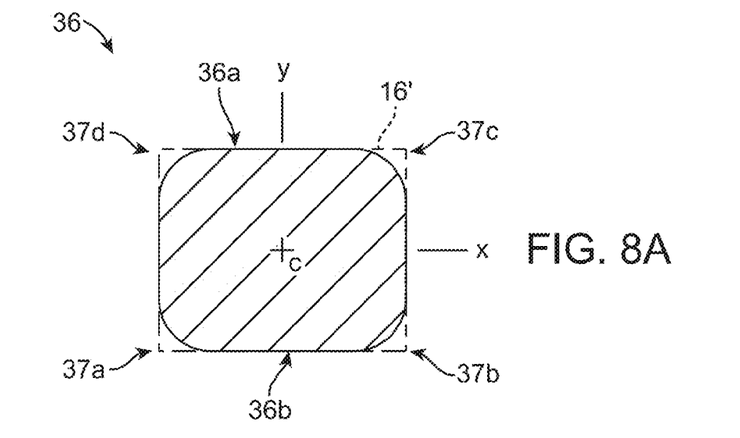
FIG. 8A shows a first type of shaped scaffold strut.

An example of the first type of shaped strut is illustrated in FIG. 8A. According to these embodiments the shaped strut 36 has retained the rectangular shape of the strut 16 from FIG. 7, except at one or more of the corners. One, two, three or all four of the sharp or right-angle corners of the strut 16 are replaced by rounded or smoothed corners for the shaped strut 36. The surfaces 36a and 36b correspond to the luminal and abluminal surfaces of the strut, respectively. FIG. 8A shows the case where the shaped strut 36 has four rounded corners 37a-37d (the phantom line 16' refers to the original shape of the strut before it was re-shaped, i.e., strut 16 from FIG. 6). The shaped strut 36 of FIG. 8A is symmetric about two orthogonal axes X and Y centered at the centroid (C) of the strut 16 or the strut 36.

Figure 8B:
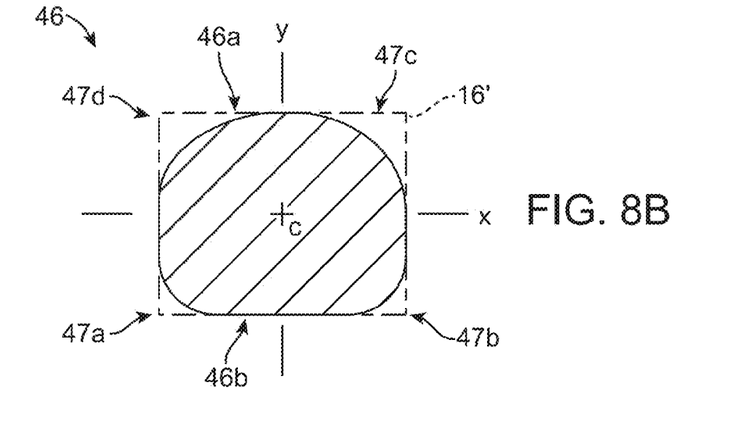
FIG. 8B shows a second type of shaped scaffold strut.

An example of the second type of shaped strut is illustrated in FIG. 8B. According to these embodiments one, both or none of the corners bordering the abluminal surface 36b have rounded corners 47a, 47b. The opposite corners 47c, 47d bordering the luminal surface 46a are rounded to a much greater extent than corners 46a, 46b (the phantom line 16a refers to the original shape of the strut before it was re-shaped, i.e., strut 16' from FIG. 6). The shaped strut 46 is symmetric about only one of two orthogonal axes; the shaped strut 46 is symmetric about an axis passing through and normal (or at a right angle) to both the abluminal and luminal surfaces 46a, 46b; and/or the shaped strut 46 is symmetric about the Y axis, but not the X axis of FIG. 8B, where the X and Y axes are centered at the centroid (C) of the strut 16 or the strut 46. The second strut type has these one-axis symmetries when the curvatures 47c, 47d are similar to each other and existing on only the luminal side of the strut; in other words, the portion to the right of the Y axis is a mirror image of the portion to the left of the Y axis.

In some embodiments the corners 47c, 47d are rounded (as shown) and may be described by a radius of curvature or radius. In these embodiments the radius of curvature for the corners 47c, 47d are about 1.5, 2, 2.5 or between 1.5 to 3 times higher than the radius of curvature for a rounded corner 47a and/or 47b. In some embodiments the corners 47c, 47d are replaced by relatively straight, sloped surfaces of between about 30, 45, 30-60, 50-80, 70 and 60 degrees measured relative to the X axis. In some embodiments, at least ½ of the flat sidewall surface of the strut is maintained when the strut is being shaped; in other words, at least ½ of the wall thickness is maintained as when cut so that not too much material is removed as to significantly weaken the strut.

Figure 8C:
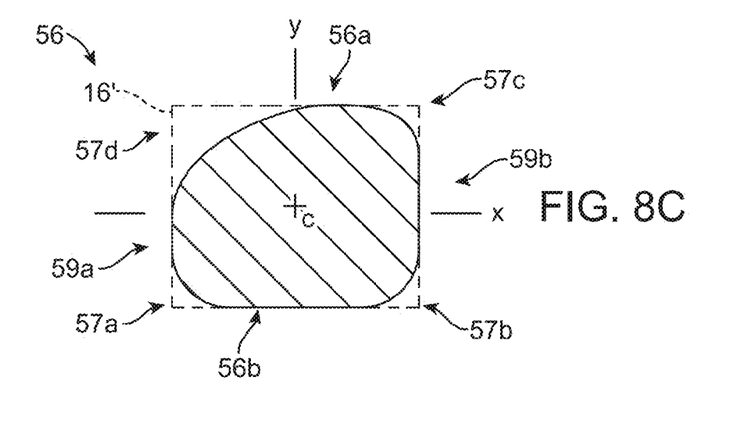
FIG. 8C shows a third type of shaped scaffold strut.

An example of the third type of shaped strut is illustrated in FIG. 8C. According to these embodiments one, two or none of the corners bordering the abluminal surface 56b have rounded corners 57a, 57b. One or both of the opposite corners 57c, 57d bordering the luminal surface 56a are rounded to a much greater extent than are corners 56a, 56b (the phantom line 16' refers to the original shape of the strut before it was re-shaped, i.e., strut 16 from FIG. 6). The shaped strut 56 is asymmetric about the Y axis and the X axis of FIG. 8C, where the X and Y axes are centered at the centroid (C) of the strut 16 or the strut 46. The third strut type may be thought of as a strut cross-section having no axes of symmetry relative to the centroid of the strut 16.

In some embodiments the corner 57c is similar to rounded corners 57a and/or 57b. The corner 57d is sloped, rounded or shaped to a much greater extent than any of corners 57a, 57b and 57c. The difference in shape between corners 57c and 57d produces the asymmetric shape for strut 56 about the Y axis. Corner 57c when curved may be described by a radius of curvature or radius. In these embodiments the radius of curvature for the corner 57d is about 1.5, 2, 2.5, 3, 4, 5 or between 1.5 to 5 times higher than the radius of curvature for a rounded corner 47a and/or 47b, and/or corner 57b. In some embodiments the corners 57c, 57d are replaced by relatively straight, sloped surfaces of between about 30 to 40, or 45 and 60 degrees measured relative to the X axis.

In some embodiments the third type of strut's leading edge (i.e. upstream side of the strut which first encounters blood flow) is thicker or retains a greater percentage of the strut 16' thickness (prior to shaping the strut) than an opposing trailing edge. This may be defined as a larger strut thickness, or amount of material, to the right (upstream side) of axis y compared to the downstream side. For example, the leading edge has 70% to 95% of the strut thickness after it being made into a shaped strut whereas the trailing edge has between 30% to 60%, or between 50% to 80% of this strut thickness (prior to the strut being shaped both the leading and trailing edges have about the same thickness). For example, in FIG. 8C the leading edge 59b is about 50% greater in terms of its straight edge length and area upstream of axis Y than compared with the trailing edge 59a. In some embodiments the shaped strut may have a constant (linear) taper or a curved (non-linear) taper from leading to trailing edges. The curved taper is shown in FIG. 8C. Alternatively the curved slope can instead be straight, which would show the constant taper embodiment.

According to another aspect of the disclosure, flame polishing is used to produce at least the first and second types of strut cross sections, e.g., struts 36 and 46 illustrated in FIGS. 8A and 8B, respectively. Flame polishing is a known method of polishing a material, usually thermoplastics or glass, by exposing it to a flame or heat. When the surface of the material is melted by the flame, surface tension of the flowing molten material causes the sharp corners of the strut 16 to smooth or round-out, thereby producing rounded corners 37a-37d, 47a-47d or 57a-57d (FIGS. 8A-8C).

"Flame polishing" of a scaffold strut as used herein means smoothing out a surface of the strut using a torch burning a fuel, e.g., hydrogen, methane, ethane, propane, or an alcohol. The fuel is combined with an oxidizer such as air or oxygen. The torch flame is placed adjacent to the surface of the scaffold such that the scaffold surface is heated to melting by both convection and radiation. In some embodiments a hydrogen/oxygen flame is used to melt the scaffold surface when desirous to take advantage of this flame chemistry, which produces no contaminates affecting the composition of the polymer surface. On the other hand, it may be advantageous to use a flame chemistry that will deposit a material onto the polymer surface. Adjustment of the fuel to oxidizer ratio results in lean or rich ratios. Rich ratios can deposit a carbonaceous layer onto the scaffold surface. This deposit can serve multiple purposes. It can help control the degree of melting by acting as an insulator. Carbonaceous deposits can also enhance hemocompatibility. Different fuels and flame chemistries have different adiabatic flame temperatures. Selection of the appropriate temperature flame will make the smoothing process more controllable and avoid excessive melting.

Another potential benefit to the flame chemistry on the surface of the bioresorbable scaffold is its effect on adhesion. Typically, a coating of a bioresorbable polymer combine with a therapeutic agent is applied to all, or a portion of, the surface of the bioresorbable scaffold. A flame treatment can oxidize a surface, increase its surface free energy, and improve the adhesion of a subsequently applied coating.

TABLE 1 below provides an example of the processing parameters that may be used to shape struts that are substantially or completely made from a blend of polylactide (PLA) and a PLA and polycaprolactone (PCL) random copolymer (e.g., 5-30% PCL) and the blended PLA-PCL combination has between about 1% to 8% by weight PCL; or the tube comprises substantially poly(L-lactide) PLLA.

TABLE 1

| Processing Parameter | Range | explanation |
| --- | --- | --- |
| Temperature in the flame | 1500-5000 C. | |
| Fuel | Methane, ethane, propane, butane, pentane, hexane, heptane, octane, nonane, decane, hydrogen, methanol, ethanol, acetylene, gasoline, kerosene, fuel oil | Fuel type clean or dirty? |
| Oxidizer/fuel stoichiometry Mass oxidizer/mass fuel | Ratio may be plus or minus 30% of stoichiometric value | |
| Speed | 0.5-30 mm/sec | Rate at which flame is passed over strut |
| Flame distance | 2-40 mm | Flame distance from the surface of the strut |
| Flame size | 2-20 mm | The length of the flame |

Some or all of the above operating parameters may be used to polish. For example, a flame temperature can be controlled and distance from the surface of the strut monitored, and/or the surface temperature of the strut can be monitored while it is exposed to the flame.

U.S. Pat. No. 8,580,180 discloses methods for shaping stent struts using heat radiated from a heat source to melt the surface of the strut. The present method of flame polishing however differs from this prior art radiated-heat method in the following way. First, the energy transfer to the strut according to U.S. Pat. No. 8,580,180 is principally from the infra-red (IR) band. A flame placed adjacent the strut transfers energy over a much broader spectrum of electromagnetic radiation. Additionally, the flame transfers heat by both a convective and radiative process. The result is that the surface chemistry of the strut may be altered when flame polishing is used. Radiative heating where the polymer temperature does not greatly exceed the melting point (of a crystalline polymer) does not alter the surface chemistry. This is especially true if the radiative heating is performed in an inert atmosphere.

Figure 9:
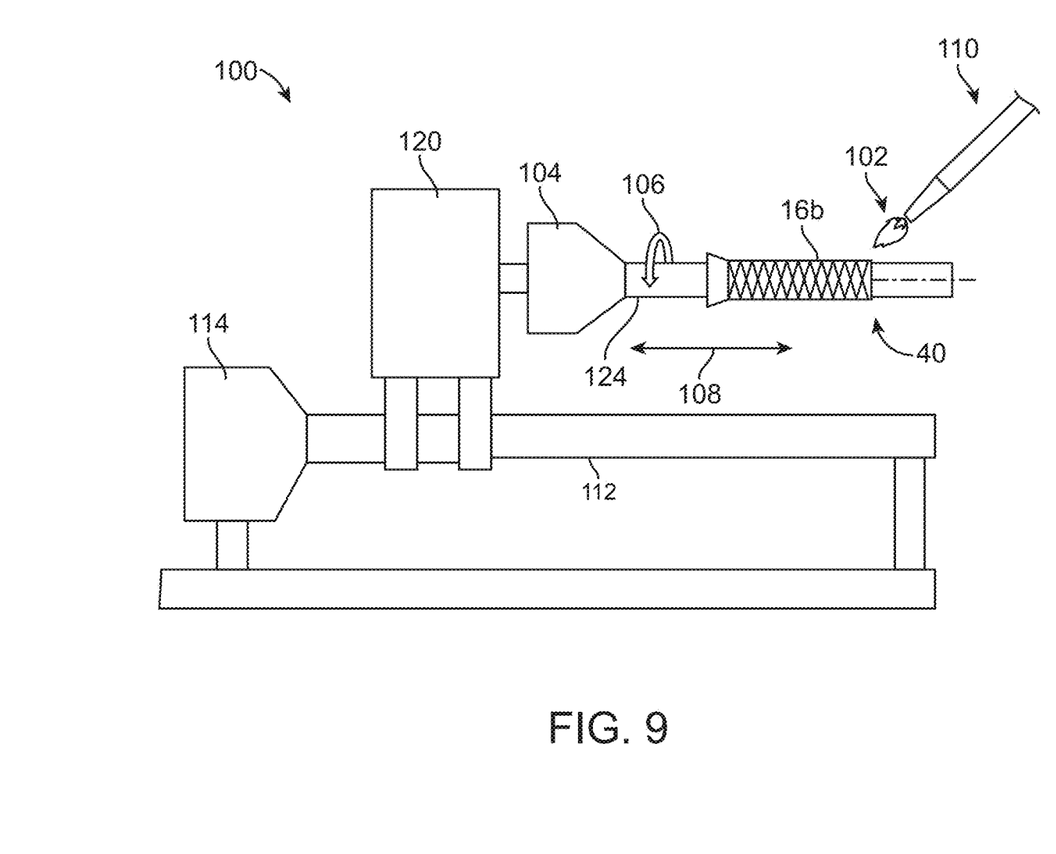
FIG. 9 is a schematic view of an apparatus for making one or more of the shaped struts of FIGS. 8A-8C using a torch.
Figure 10A:
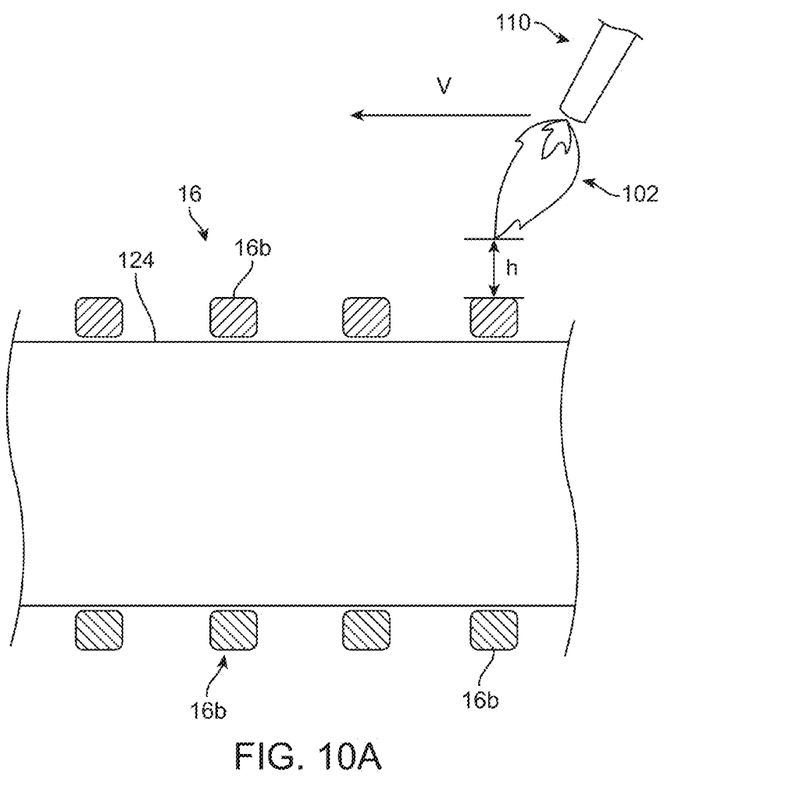
FIG. 10A is a close-up view of a process for making a shaped strut by passing a flame of the torch over the external surface of the scaffold.
Figure 10B:
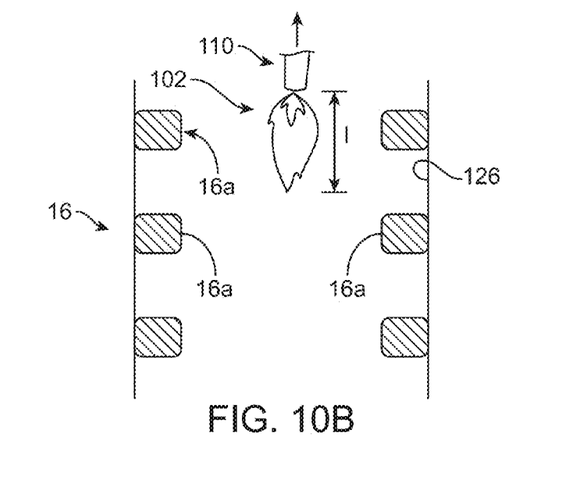
FIG. 10B is a close-up view of a process for making a shaped strut by passing a flame of the torch through the bore of the scaffold.

FIGS. 9, 10A, and 10B depict aspects of an apparatus and method for flame polishing a scaffold according to the disclosure. FIGS. 9 and 10A depict methods for exposing primarily the abluminal surfaces 16b of the scaffold struts 16 to a torch 110 having a flame 102. According to these embodiments, the scaffold 40 is held by a cylindrical mandrel 124 which passes through the center of the scaffold 40. The mandrel 124 is removably mounted via a holder 104 to motor 120. Motor 120 is movably mounted on a linear rail 112 of a translational stage 114. Apparatus 100 may be configured via numerical control to move the scaffold 40 relative to the torch 110 at a precisely controlled distance and length of time to ensure the scaffold is not damaged during polishing. Relative motion includes a combination of rotational motion 106 and axial translation 108. Rotational motion 106 is accomplished by rotation of mandrel 124 by motor 120. Axial translation 108 is accomplished by sliding mandrel 124 together with motor 120 on rail 112. The numeric control may control the motor 120 and translational stage 114 to precisely control the relative motion.

Referring to FIG. 10A, a portion of the scaffold struts 16 are shown on the mandrel 124. The vertical distance (h) and rate (v) at which the flame 102 passes over the abluminal surface dictates the degree to which the surface of the struts are re-shaped by the flame. The process may be controlled by monitoring these values. Alternatively, the surface temperature of the struts may be monitored when the flame is passed over (or under) the struts. According to the embodiments the torch 110 is placed at the distance (h) from the struts 16 and moved at the rate (v) over the scaffold abluminal (and/or the scaffold abluminal surface moved under the stationary torch 110) to cause surface melting, flow, and shaping that rounds out the corners bordering or edges of the abluminal surface portion of struts 16, thereby making shaped struts. TABLE 1 provides examples of processing parameters including the rate (v), distance (h) and the flame size (I) (FIG. 10B).

Referring to FIG. 10B an apparatus is used to hold the scaffold within a hollow chamber 126 or sits atop a platform, e.g., a ceramic or glass chamber/platform. Either configuration includes an opening to allow the flame 102 to be passed through the bore or lumen of the scaffold as indicated in FIG. 10B, either manually or under numeric machine control. The torch passes closer to the luminal surface 16a and shapes this surface by surface tension more so than the abluminal surface. By placing the flame closer to the luminal surface the corners bordering or edges of the luminal surface are expected to round out more than the corners or edges of the abluminal surface.

According to one embodiment the scaffold 40 is placed on the mandrel 124 and the torch 110 passed over the scaffold 40 to produce rounded corners 37a and 37b. The scaffold is then placed within a tubular, open-ended chamber 126 (or atop a platform having an opening for passage of the torch through the scaffold bore) and the torch 110 passed through the scaffold bore to round corners, e.g., corners 37c and 37d. The exposure time to the flame 102 when the flame 102 is passed through the scaffold bore may be approximately the same as, or slightly longer than when the flame is 102 passed over the exterior of the scaffold 40 (FIG. 9). The flame utilized in FIG. 10B may be similar in size, or considerably smaller, than the flame used in apparatus 100. When the luminal surface 16a is exposed to the flame for a longer period of time than was the abluminal surface 16b, one may produce the second type of shaped strut 46 (symmetric about only one axis, e.g., the Y-axis in FIG. 8B). When the luminal surface 16a is exposed to the flame for the same period of time as the abluminal surface 16b, one may produce the first type of shaped strut 36 (symmetric about two axes, e.g., the X and Y axes in FIG. 8A)

According to another aspect of the disclosure a brush is used to produce the shaped struts 36, 46 and/or 56. The brush has bristles configured or adapted to abrade the surface of the scaffold struts. As will be appreciated, the brush may be moved in one direction only over the strut 16 surface to produce the shaped strut 56, or equally in opposite directions to produce the shaped struts 36 and 46.

The brush bristles or wires have a diameter preferably smaller than the width (w) and/or thickness (t) of the strut 16. The bristle material has a much higher hardness than the surface of the strut. The sides of the wires may be smooth. However, it is advantageous if the sides of the wires themselves have a roughness so that they may abrade the strut material. The ends of the wires may have smooth, rounded tips or tips with sharp edges. The brush wires may have one or more, or any combination of the following properties:

The wire length (from stem to tip) is between 500 and 8000 microns.

The mean roughness (Ra) of the wire is between 0.1 and 20 microns.

The wire material is metal, metal alloy, polymer, polymer containing an abrasive, ceramic, or glass.

The wire diameter is between about 1 to 200 microns, about 2 to 150 microns or between about 10 to 100 microns.

The wires of the brush may be relatively short so that the abrasion of the scaffold surface occurs mostly from the tips scrapping over the surface of the strut. Alternatively, the wires may be longer but have a higher side wall surface roughness. In this case the wires abrade the surface of the strut when sliding over the strut.

Figures 11, 12A, 12B:
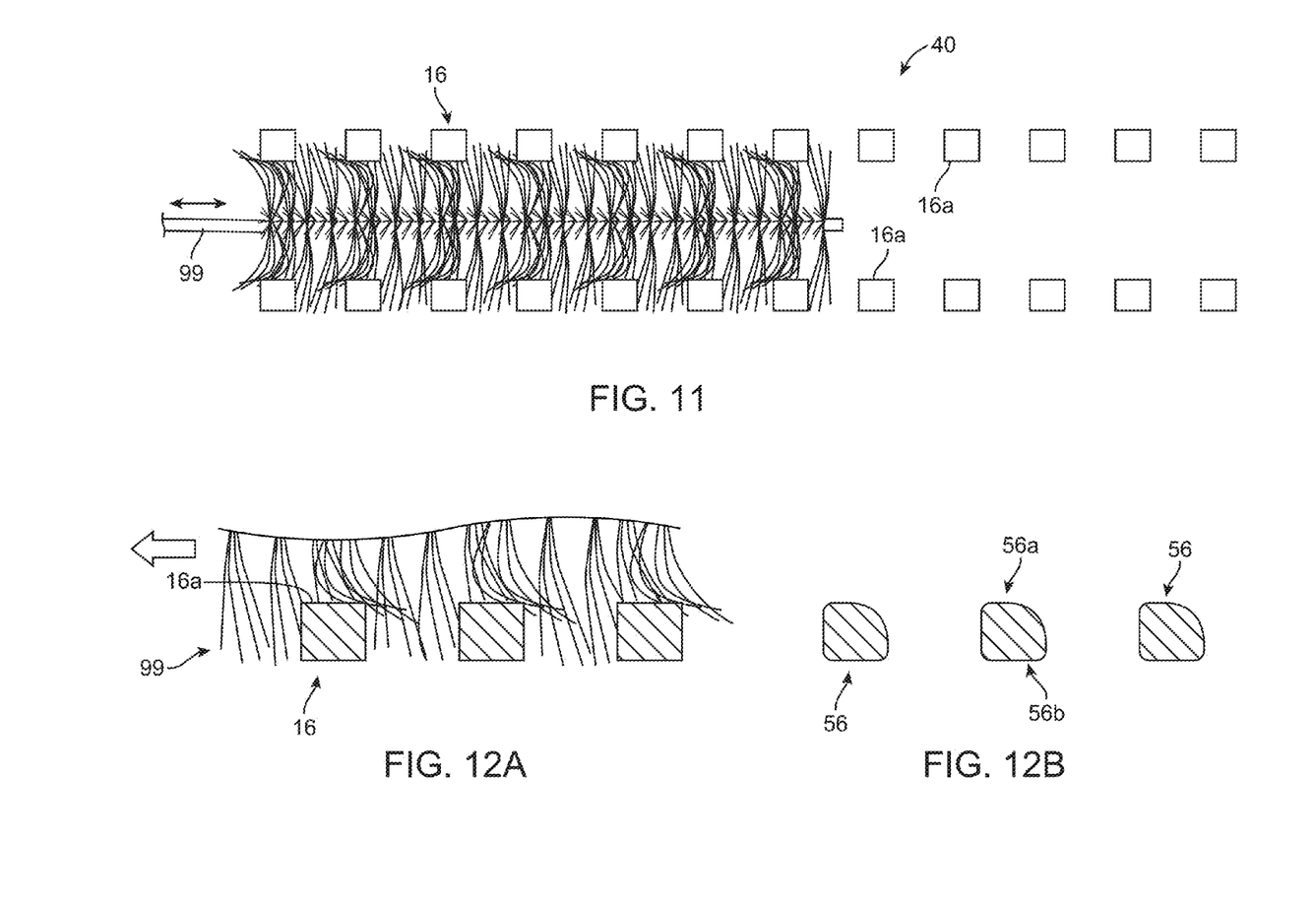
FIG. 11 is a side cross-sectional view of a scaffold while a brush is being pulled or pushed through the scaffold bore. The brush is being used to make one or more of the shaped struts of FIGS. 8A-8C.
FIG. 12A is a close-up view showing the brush of FIG. 11 being pulled or pushed over the surfaces of scaffold struts.
FIG. 12B is a close-up view showing the shaped struts of FIG. 8C produced by the brushing method in FIG. 12A.

FIG. 11 depicts an example of using a brush 99 to shape the corners or edges bordering the luminal surfaces of struts. The brush resembles a pipe brush sized appropriately to abrade the corners or edges of the luminal surfaces of the scaffold as the brush 99 is pulled or pushed through the scaffold bore. FIGS. 12A and 12B depicts a close up view of the brush 99 when the brush 99 is first applied to the struts 16 and after the brush has been applied. The brush direction predominately moved over the struts 16 in the direction shown to produce the shaped strut 56. Additionally the brush may be used on the other surfaces as well to round out corners. The brush may lie on a wire which extends completely through the bore of the scaffold to facilitate pulling the brush through the scaffold bore.

Figure 13:
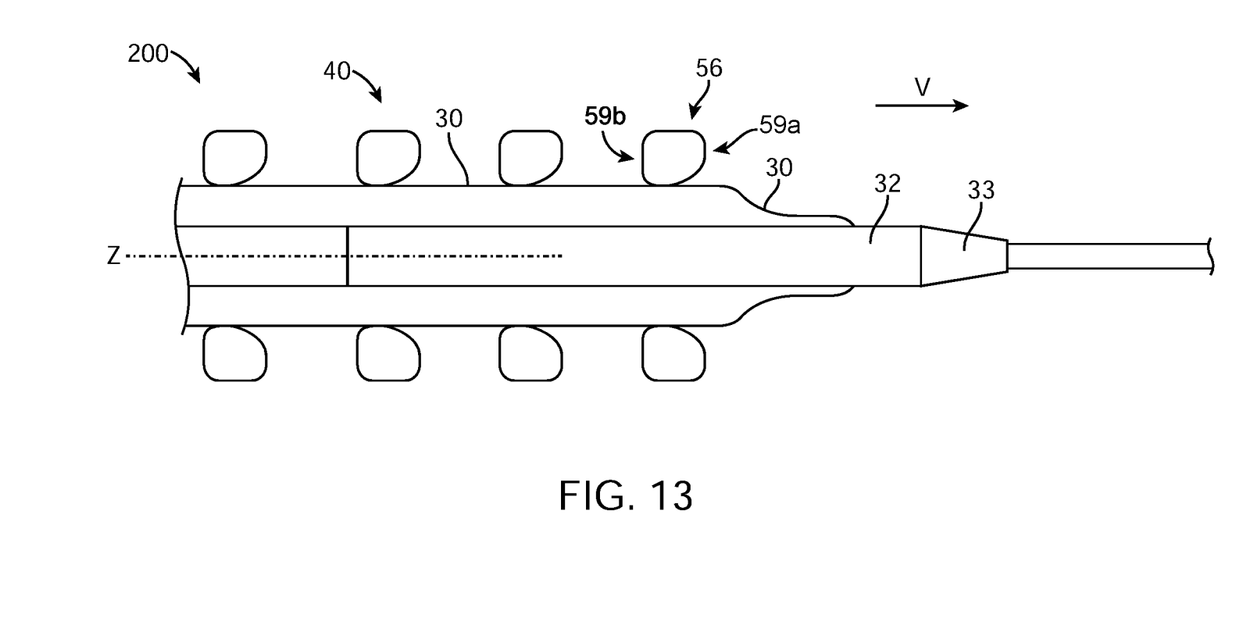
FIG. 13 is a partial side-cross-sectional view of a medical device distal end showing a scaffold crimped to a balloon of a balloon catheter. The scaffold struts have the shaped struts of FIG. 8C. The direction of blood flow (from a proximal to distal end of the catheter) when the scaffold is being implanted is indicated by "V."

FIG. 13 depicts a partial side cross-sectional view of a distal end portion of a medical device 200 according to another aspect of the disclosure. The medical device 200 includes the scaffold 40 having shaped struts 56 crimped to a balloon 30 of a balloon catheter (the catheter has a shaft 32 providing an inflation lumen for the balloon 30 and a distal tip 33), as depicted in FIG. 13. The scaffold has the third type of shaped struts, shaped struts 56, arranged such that the leading edge 59b (FIGS. 13 and 8C) of a shaped strut 56 is located upstream of the trailing edge 59a. By having the struts shaped and arranged in this manner it is believed that the hemocompatibility of the scaffold can be greater improved during the initial stages of patency. The orientation of the strut 56 with a downward-sloped corner 56d providing the tapered trailing edge 59a to the strut 56 assists with reducing the amount of blood recirculation downstream of the strut. In other embodiments the scaffold has the second type of shaped strut 46, with sloped surfaces 47c, 47d in place of surfaces 57c, 57d. The sloped surfaces 47c, 47d face the balloon surface 30.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

The invention claimed is:

1. A medical device, comprising:
    a balloon catheter including a balloon located at a distal end and a distal tip; and
    a polymer scaffold crimped to the balloon, the scaffold having a pattern of shaped struts, wherein a shaped strut has a leading edge, a trailing edge, a luminal surface facing a surface of the balloon and an abluminal surface facing away from the balloon surface;
    wherein the shaped strut is, in respect to a cross-section of the strut, asymmetric about each of two orthogonal axes passing through a centroid of the strut cross-section; and
    wherein the shaped strut further includes a linear or non-linear taper from the leading to the trailing edge thereof such that a strut thickness at the trailing edge is less than the strut thickness at the leading edge; and
    wherein the shaped strut leading edge is located a first distance from the distal tip, the shaped strut trailing edge is located a second distance from the distal tip, and the first distance is greater than the second distance.

2. The medical device of claim 1, wherein the strut thickness at the trailing edge is between about 20% and 60% of the strut thickness at the leading edge.

3. The medical device of claim 2, wherein the shaped struts have an aspect ratio (AR) of strut width to strut thickness between 1 and 4.

4. The medical device of claim 3, wherein a maximum thickness of the strut is between 80 microns and 120 microns.

5. The medical device of claim 4, wherein the scaffold is substantially or completely made from a blend of polylactide (PLA) and a PLA and polycaprolactone (PCL) random copolymer (e.g., 5-30% PCL) and the blended PLA-PCL combination has between about 1% to 8% by weight PCL.

6. The medical device of claim 4, wherein the scaffold is substantially or completely made from poly(L-lactide) PLLA.

7. The medical device of claim 1, wherein the scaffold is orientated on the balloon so that the shaped strut leading edge is upstream of the shaped strut trailing edge when the scaffold is being implanted at a treatment site.

8. The medical device of claim 1, wherein the shaped strut comprises a radius of curvature for a corner of the luminal surface and a corner of the abluminal surface, and wherein the radius of curvature at the luminal surface corner is about 3 times higher than the radius of curvature at the abluminal surface corner.

9. A medical device, comprising:
    a balloon catheter including a balloon, a distal end and a distal tip; and
    a scaffold crimped to the balloon, wherein the scaffold is made from a tube and the tube is substantially or completely made from a blend of polylactide (PLA) and a PLA and polycaprolactone (PCL) random copolymer (e.g., 5-30% PCL) and the blended PLA-PCL combination has between about 1% to 8% by weight PCL;

the scaffold including a shaped strut, wherein the shaped strut has a leading edge, a trailing edge, a luminal surface facing a surface of the balloon and an abluminal surface facing away from the balloon surface;

wherein a cross-section of the shaped strut is asymmetric about each of two orthogonal axes passing through a centroid of the strut cross-section, such that a strut thickness at the trailing edge is between 30% and 80% of the strut thickness at the leading edge;

wherein the shaped strut leading edge is located a first distance from the distal tip, the shaped strut trailing edge is located a second distance from the distal tip, and the first distance is greater than the second distance.

10. The medical device of claim 9, wherein the tube from which the scaffold was made has a wall thickness, and wherein the strut thickness at the leading edge is between 70% to 95% of the wall thickness.

11. The medical device of claim 9, wherein the tube from which the scaffold was made has a wall thickness, and wherein the strut thickness at the trailing edge is between 30% and 60% of the wall thickness.

12. The medical device of claim 9, wherein a corner of the trailing edge located on the luminal surface of the shaped strut has a higher slope than a corner of the leading edge located on the abluminal surface of the shaped strut.

13. A medical device, comprising:

a balloon catheter including a balloon, a distal end and a distal tip; and a scaffold crimped to the balloon, wherein the scaffold is made from a tube having a wall thickness, and the tube is substantially or completely made from a blend of polylactide (PLA) and a PLA and polycaprolactone (PCL) random copolymer (e.g., 5-30% PCL) and the blended PLA-PCL combination has between about 1% to 8% by weight PCL; and the scaffold further comprising ring elements formed by struts connected at strut junctions, the struts including shaped struts located at the strut junctions, wherein a shaped strut comprises a leading edge, a trailing edge, a luminal surface facing a surface of the balloon and an abluminal surface facing away from the balloon surface, the shaped strut further comprising:

a cross-section asymmetric about each of two orthogonal axes passing through a centroid of the cross-section, a leading edge thickness between 70% to 95% of the wall thickness, a trailing edge thickness between 30% and 60% of the wall thickness, a radius of curvature for a corner of a luminal surface is about 4 times higher than a radius of curvature for a corner of an abluminal surface; and wherein the shaped strut leading edge is located a first distance from the distal tip, the shaped strut trailing edge is located a second distance from the distal tip, and the first diameter is greater than the second distance.

* * * * *